United States Patent
Lee et al.

(10) Patent No.: US 11,062,800 B2
(45) Date of Patent: *Jul. 13, 2021

(54) METHOD FOR MANAGING ANNOTATION JOB, APPARATUS AND SYSTEM SUPPORTING THE SAME

(71) Applicant: Lunit Inc., Seoul (KR)

(72) Inventors: Kyoung Won Lee, Seoul (KR); Kyung Hyun Paeng, Busan (KR)

(73) Assignee: LUNIT INC., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/814,131

(22) Filed: Mar. 10, 2020

(65) Prior Publication Data

US 2020/0210926 A1   Jul. 2, 2020

Related U.S. Application Data

(63) Continuation of application No. PCT/KR2018/013664, filed on Nov. 9, 2018.

(51) Int. Cl.
  *G16H 30/40* (2018.01)
  *G06K 9/62* (2006.01)
  (Continued)

(52) U.S. Cl.
  CPC .......... *G16H 30/40* (2018.01); *G06F 40/169* (2020.01); *G06K 9/6262* (2013.01); *G06N 3/08* (2013.01);
  (Continued)

(58) Field of Classification Search
  CPC .............................. G06F 40/169; G06F 40/56
  See application file for complete search history.

(56) References Cited

U.S. PATENT DOCUMENTS 10,025,902 B2 * 7/2018 Barral ............... G16H 50/20
10,140,421 B1   11/2018 Bernard et al.
(Continued)

FOREIGN PATENT DOCUMENTS

JP   2006-252541   9/2006
JP   2016-049327   4/2016
(Continued)

OTHER PUBLICATIONS

USPTO, Office Action of U.S. Appl. No. 16/671,430, dated Sep. 29, 2020.
(Continued)

*Primary Examiner* — Reginald R Reyes
(74) *Attorney, Agent, or Firm* — Lex IP Meister, PLLC

(57) ABSTRACT

A computing device obtains information about a medical slide image, and determines a dataset type of the medical slide image and a panel of the medical slide image. The computing device assigns to an annotator account, an annotation job defined by at least the medical slide image, the determined dataset type, an annotation task, and a patch that is a partial area of the medical slide image. The annotation task includes the determined panel, and the panel is designated as one of a plurality of panels including a cell panel, a tissue panel, and a structure panel. The dataset type indicates a use of the medical slide image and is designated as one of a plurality of uses including a training use of a medical learning model and a validation use of the machine learning model.

18 Claims, 24 Drawing Sheets

(51) Int. Cl.

| | | |
|---|---|---|
| *G06N 3/08* | (2006.01) | |
| *G16H 30/20* | (2018.01) | |
| *G06F 40/169* | (2020.01) | |
| *G16H 40/20* | (2018.01) | |
| *G16H 10/40* | (2018.01) | |
| *G06Q 10/06* | (2012.01) | |
| *G06T 7/00* | (2017.01) | |

(52) U.S. Cl.
CPC ............... *G06Q 10/06395* (2013.01); *G06Q 10/063112* (2013.01); *G06T 7/0012* (2013.01); *G16H 10/40* (2018.01); *G16H 30/20* (2018.01); *G16H 40/20* (2018.01); *G06T 2207/20081* (2013.01); *G06T 2207/30024* (2013.01); *G06T 2207/30096* (2013.01)

(56) References Cited

U.S. PATENT DOCUMENTS

| | | |
|---|---|---|
| 10,755,411 B2 | 8/2020 | Zhang |
| 2009/0185731 A1 | 7/2009 | Ray et al. |
| 2012/0210204 A1 | 8/2012 | Kramer et al. |
| 2013/0129252 A1 | 5/2013 | Lauper et al. |
| 2014/0219548 A1 | 8/2014 | Wels et al. |
| 2015/0086133 A1 | 3/2015 | Grady |
| 2015/0089337 A1 | 3/2015 | Grady |
| 2015/0119289 A1 | 4/2015 | Chen et al. |
| 2016/0063700 A1 | 3/2016 | Itai |
| 2016/0350919 A1 | 12/2016 | Steigauf et al. |
| 2016/0364526 A1 | 12/2016 | Reicher et al. |
| 2017/0236271 A1 | 8/2017 | Kim et al. |
| 2018/0031817 A1 | 2/2018 | Barral |
| 2018/0046759 A1 | 2/2018 | Barral |
| 2018/0137244 A1 | 5/2018 | Sorenson et al. |
| 2018/0260954 A1 | 9/2018 | Jung et al. |
| 2018/0276815 A1 | 9/2018 | Xu et al. |
| 2019/0251694 A1 | 8/2019 | Han et al. |
| 2020/0152316 A1* | 5/2020 | Lee ..................... G16H 50/20 |
| 2020/0161005 A1 | 5/2020 | Lyman et al. |

FOREIGN PATENT DOCUMENTS

| | | |
|---|---|---|
| KR | 10-2009-0006295 | 1/2009 |
| KR | 10-2014-0093974 | 7/2014 |
| KR | 10-2016-0012114 | 2/2016 |
| KR | 10-1623431 | 5/2016 |
| KR | 10-2017-0046104 | 4/2017 |
| WO | 2014/153423 | 9/2014 |

OTHER PUBLICATIONS

USPTO, Office Action of U.S. Appl. No. 16/671,430 dated Jul. 15, 2020.

EPO, Supplementary European Search Report of EP 18939311.9 dated Apr. 13, 2021.

Zhu, Wentao, Qi Lou, Y. S. Van and X. Xie. "Deep Multi-instance Networks with Sparse Label Assignment for Whole Mammogram Classification." MICCAI (2017). (Year: 2017).

USPTO, Office Action of U.S. Appl. No. 16/671,430 dated May 13, 2021.

* cited by examiner

NUCLEAR GRADE 1  NUCLEAR GRADE 2  NUCLEAR GRADE 3  LYMPHOCYTE  MITOSIS  FIBROBLAST

METHOD FOR MANAGING ANNOTATION JOB, APPARATUS AND SYSTEM SUPPORTING THE SAME

CROSS-REFERENCE TO RELATED APPLICATION

This application is a continuation of PCT Application No. PCT/KR2018/013664 filed on Nov. 9, 2018, the entire contents of which are incorporated herein by reference.

BACKGROUND

(a) Field

The present disclosure relates to an annotation job management method, an apparatus and a system supporting the same. In particular, the present disclosure relates to a method for managing annotation job more efficiently and ensuring accuracy of annotation results, and an apparatus and a system for supporting the method.

(b) Description of the Related Art

As shown in FIG. 1, supervised learning is a machine learning method for constructing a target model 3 for performing a target task by learning a dataset 2 having label information (that is, correct answer information). Therefore, in order to perform the supervised learning on a dataset 1 which doesn't have label information (indicated by a tag icon), annotation job should precede.

The annotation job means a job of tagging label information for each data to generate a training dataset. Since the annotation job was generally performed manually, a considerable amount of human cost and time cost is consumed for generating a large amount of training dataset. In particular, in case of building a machine learning model for detecting the location of lesions or determining the lesion types in medical images, the annotation job should be performed by a skilled practitioner, which is much more expensive than other domains.

In the past, the annotation job was not performed according to a systematic process. For example, in the conventional method, to determine whether to perform an annotation, an administrator identifies the characteristics of medical images with eyes, classifies the medical images manually, and then assigns each medical image to an appropriate annotator. In addition, in the related art, the administrator designates a region for annotation on a medical image, and then assigns a task to an annotator. That is, various processes such as medical image classification, job assignment, annotation region designation, and the like are manually performed by an administrator, which causes a considerable amount of time cost and human cost to be consumed for the annotation job.

Furthermore, although the machine learning technique itself has been sufficiently advanced, there have been many difficulties in applying machine learning techniques to various fields due to the time and cost problems of the annotation job.

Therefore, in order to increase the usability of machine learning techniques, a method for performing annotation more efficiently and systematically is required.

SUMMARY

Some embodiment of the present disclosure provide a method for more efficiently and systematically performing and managing annotation job through annotation job automation, and an apparatus and system supporting the method.

Some embodiments of the present disclosure provide a data design product or a data modeling product that can systematically manage annotation jobs.

Some embodiments of the present disclosure provide a method for automatically assigning an annotation job to an appropriate annotator, and an apparatus and system supporting the method.

Some embodiments of the present disclosure provide a method for automatically extracting a patch image where an annotation job is performed from a medical slide image, and an apparatus and system supporting the method.

Some embodiments of the present disclosure provide a method for ensuring the accuracy of annotation results, and an apparatus and system supporting the method thereof.

It should be noted that objects of the present disclosure are not limited to the above-described object, and other objects of the present disclosure will be apparent to the person of ordinary skill in the art from the following descriptions.

According to an embodiment of the present invention, an annotation job management method performed by a computing device may be provided. The method may include obtaining information about a medical slide image, determining a dataset type of the medical slide image and a panel of the medical slide image, and assigning to an annotator account, an annotation job defined by at least the medical slide image, the determined dataset type, an annotation task and a patch that is a partial area of the medical slide image. The annotation task may include the determined panel, and the panel may be designated as one of a plurality of panels including a cell panel, a tissue panel, and a structure panel. The dataset type may indicate a use of the medical slide image and may be designated as one of a plurality of uses including a training use of a machine learning model or a validation use of the machine learning model.

In some embodiments, the annotation task may be defined to further include a task class. The task class may indicate an annotation target defined from a perspective of the panel.

In some embodiments, the plurality of uses may further include an OPT (Observer Performance Test) use of the machine learning model.

In some embodiments, determining the dataset type and panel may include inputting the medical slide image to the machine learning model and determining the dataset type and the panel based on an output value of the machine learning model.

In some embodiments, obtaining the information about the medical slide image may include detecting, by a worker agent monitoring a storage, that a file of the medical slide image is added to a designated location on the storage, inserting, by the worker agent, information about the medical slide image into a database, and obtaining the information about the medical slide image from the database.

In some embodiments, assigning to the annotator account the annotation job may include automatically assigning the annotation job to the annotator account that who is selected based on an annotation performance history associated with a combination of the dataset type of the annotation job and the panel of the annotation task.

In some embodiments, the annotation task may further include a task class. The task class may indicate an annotation target defined from a perspective of the panel. Further, assigning to the annotator account the annotation job may include automatically assigning the annotation job to the annotator account that is selected based on an annotation performance history associated with a combination of the panel and the task class of the annotation task.

In some embodiments, assigning to the annotator account the annotation job may include obtaining candidate patches of the medical slide image, inputting each of the candidate patches to the machine learning model to obtain an output value for each class, and automatically selecting a patch for the annotation job among the candidate patches based on the output value for each class.

In some embodiments, automatically selecting the patch for the annotation job may include calculating an entropy value using the output value for each class for each of the candidate patches and selecting a patch for the annotation job having the entropy value being equal to or greater than a reference value from among the candidate patches.

In some embodiments, assigning to the annotator account the annotation job may include obtaining candidate patches of the medical slide image, calculating a misprediction probability of the machine learning model for each of the candidate patches, and selecting as a patch of the annotation job a candidate patch having the calculated misprediction probability being equal to or greater than a reference value from among the candidate patches.

In some embodiments, the annotation job management method may further include obtaining a first annotation result data of the annotator account assigned the annotation job, comparing the first annotation result data with a result that is obtained by inputting a patch of the annotation job to the machine learning model, and reassigning the annotation job to another annotator account when a difference between the two results is greater than a reference value.

In some embodiments, the annotation job management method may further include obtaining a first annotation result data of the annotator account assigned the annotation job, obtaining a second annotation result data of another annotator account, and disapproving the first annotation result data when a similarity between the first annotation result data and the second annotation result data is less than a reference value.

According to another embodiment, an annotation management apparatus including a memory including one or more instructions and a processor is provided. The processor, by executing the one or more instructions, may obtain information about a medical slide image, determines a dataset type of the medical slide image and a panel of the medical slide image, and assigns to an annotator account, an annotation job which is defined by at least the medical slide image, the determined dataset type, an annotation task and a patch that is a partial area of the medical slide image. The annotation task may include the determined panel, and the panel may be designated as one of a plurality of panels including a cell panel, a tissue panel and a structure panel. The dataset type may indicate a use of the medical slide image and may be designated as one of a plurality of uses including a training use of a machine learning model and a validation use of the machine learning model.

In some embodiments, a non-transitory computer-readable medium storing a computer program is provided. The computer program, when executed by a computing device, may cause the computing device to obtain information about a medical slide image, determine a dataset type of the medical slide image and a panel of the medical slide image, and assign to an annotator account, an annotation job defined by at least the medical slide image, the determined dataset type, an annotation task and a patch that is a partial area of a medical slide image. The annotation task may include the determined panel, and the panel may be designated as one of a plurality of panels including a cell panel, a tissue panel, and a structure pane, The dataset type may indicate a use of the medical slide image and may be designated as one of a plurality of uses including a training use of a medical learning model and the validation use of a medical learning model.

According to various embodiments of the present disclosure as described above, as the annotation task is automated generally, the convenience of the administrator may be increased, and the overall work efficiency may be greatly improved. Accordingly, the time cost and human cost required for the annotation job may be greatly reduced. In addition, as the burden of annotation job is reduced, the utility of machine learning techniques may be further increased.

In some embodiment, various data associated with the annotation job may be systematically managed based on the data modeling output. As a result, data management costs can be reduced, and the overall annotation job process may be facilitated.

In some embodiment, by automatically assigning annotation jobs to appropriate annotators, the burden on the administrator may be reduced, and the accuracy of annotation results can be improved.

In some embodiment, the accuracy of the annotation results may be ensured by comparing and validating the results of annotation jobs with those of machine learning models or of other annotators. Accordingly, the performance of the machine learning model that learns the annotation results may also be improved.

In some embodiment, a patch that indicates an area where annotation is performed may be automatically extracted. Therefore, the workload of the administrator may be minimized In some embodiment, only patches effective for learning, among a plurality of candidate patches, may be selected as annotation targets based on misprediction probabilities, entropy values, and the like of the machine learning model. As a result, the amount of annotation jobs may be reduced, and a good learning dataset may be generated.

The effects of the present disclosure are not limited to those mentioned above, and other effects which have not been mentioned can be clearly understood by the person of ordinary skill in the art from the following description.

DETAILED DESCRIPTION OF THE EMBODIMENTS

Figure 1:
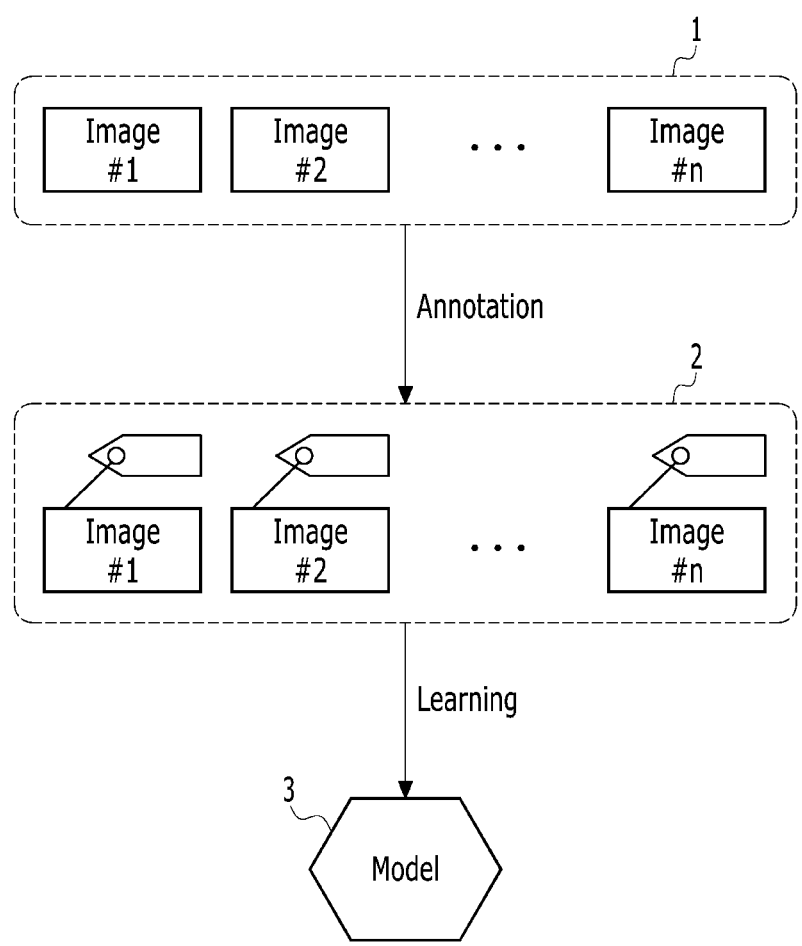
FIG.1 is an example diagram for explaining a relationship between supervised learning and an annotation job.

Hereinafter, preferred embodiments of the present disclosure will be described with reference to the attached drawings. Advantages and features of the present disclosure and methods of accomplishing the same may be understood more readily by reference to the following detailed description of preferred embodiments and the accompanying drawings. The present disclosure may, however, be embodied in many different forms and should not be construed as being limited to the embodiments set forth herein. Rather, these embodiments are provided so that this disclosure will be thorough and complete and will fully convey the concept of the disclosure to the person of ordinary skill in the art, and the present disclosure will only be defined by the appended claims. Like reference numerals designate like elements throughout the specification.

Unless otherwise defined, all terms (including technical and scientific terms) used herein have the same meaning as commonly understood by the person of ordinary skill in the art to which this disclosure belongs. Further, it will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. The terms used herein are for the purpose of describing particular embodiments only and is not intended to be limiting. As used herein, the singular forms "a", "an" and "the" are intended to include the plural forms as well, unless the context clearly indicates otherwise.

It will be further understood that, although the terms first, second, A, B, (a), (b), and the like may be used herein to describe various elements, components, steps and/or operations. These terms are only used to distinguish one element, component, step or operation from another element, component, step, or operation. Thus, a first element, component, step or operation discussed below could be termed a second element, component, step or operation without departing from the teachings of the present inventive concept. It will be further understood that when an element is referred to as being "connected to" or "coupled with" another element, it can be directly connected or coupled with the other element or intervening elements may be present.

It will be further understood that the terms "comprise" or "comprising", "include" or "including", and "have" or "having" specify the presence of stated elements, steps, operations, and/or devices, but do not preclude the presence or addition of one or more other elements, steps, operations, and/or devices.

Before description of this specification, some terms used herein will be clarified.

As used herein, the term "label information" is correct answer information of a data sample and refers to information obtained through an annotation job. The term "label" may be used interchangeably with terms such as annotation and tag.

As used herein, the term "annotation" refers to a job for tagging label information on a data sample or tagged information (i.e., annotation) itself. The term "annotation" may be used interchangeably with terms such as tagging and labeling.

As used herein, the term "misprediction probability" refers to a probability or a possibility that a prediction result includes an error (that is, a probability that a prediction is incorrect), when a specific model for a given data sample performs prediction.

Figure 10:
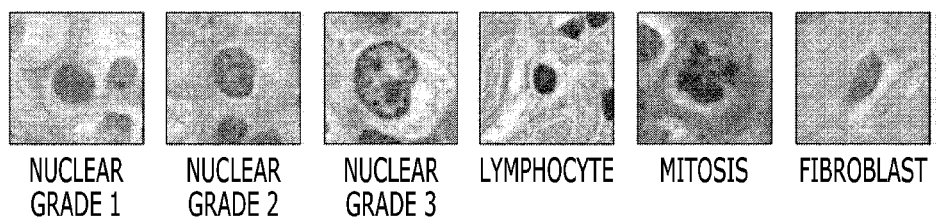
FIG. 10, FIG. 11, FIG. 12, and FIG. 13 are example diagrams for explaining a panel type determination method according to some embodiments of the present disclosure.
Figure 11:
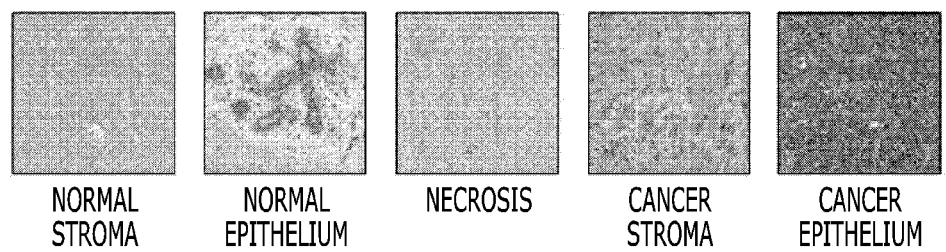
Figure 12:
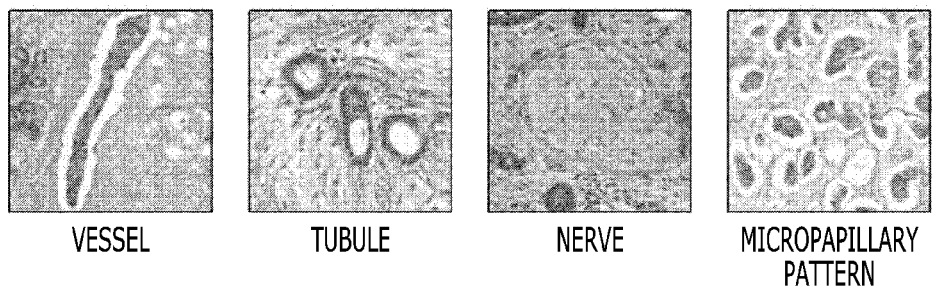

As used herein, the term "panel" refers to a type of patch to be extracted from a medical slide image or a type of the medical slide image itself. The panel may be classified into a cell panel, a tissue panel, and a structure panel, but the technical scope of the present disclosure is not limited thereto. For reference, examples of patches corresponding to each type of panels are shown in FIG. 10 to FIG. 12.

As used herein, the term "instruction" refers to a series of instructions that are grouped by function and are executed by a processor or a component of a computer program.

Hereinafter, some embodiments of the present disclosure are described in detail with reference to the accompanying drawings.

Figure 2:
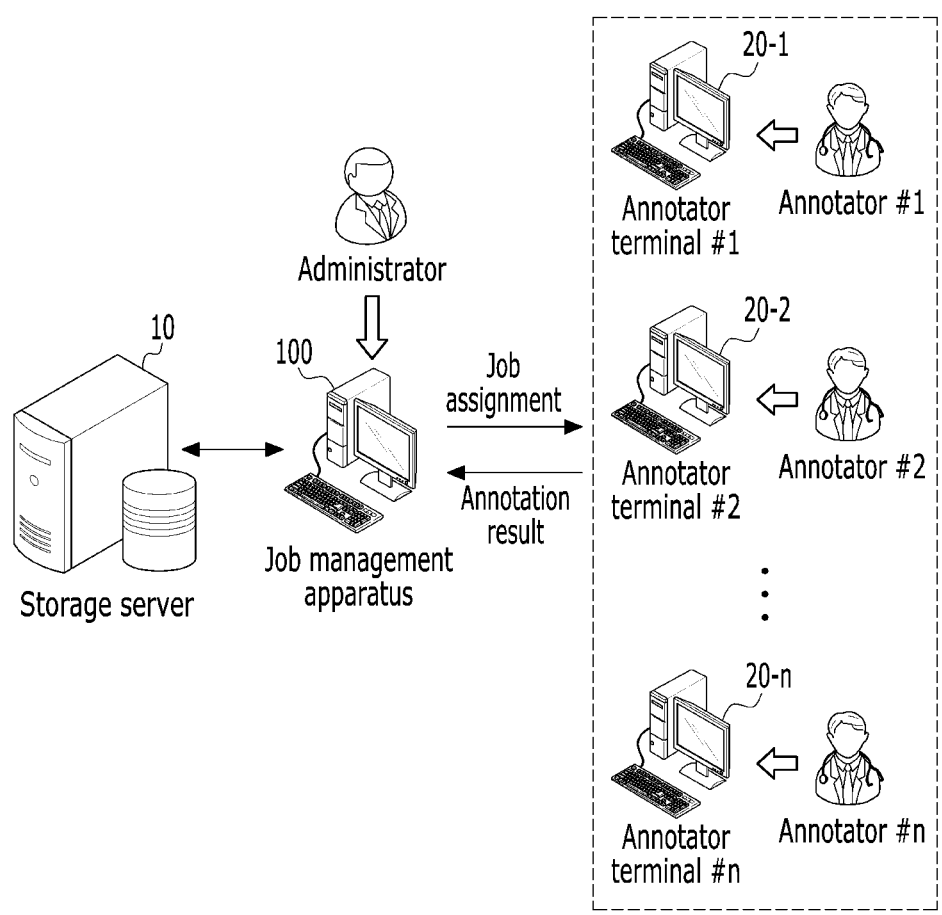
FIG. 2 and FIG. 3 are example diagrams for explaining an annotation job management system according to some embodiments of the present disclosure.

FIG. 2 is an example diagram for explaining an annotation job management system according to some embodiments of the present disclosure.

Referring to FIG. 2, an annotation job management system may include a storage server 10, one or more annotator terminals 20-1 to 20-*n*, and an annotation job management apparatus 100. However, the system shown in FIG. 1 merely corresponds to an exemplary embodiment for achieving an object of the present disclosure, and some elements may be added or omitted as necessary. For example, in some other embodiments, as shown in FIG. 3, the annotation job management system may further include a reviewer terminal 30 where review (that is, evaluation) on the annotation job is performed.

Figure 3:
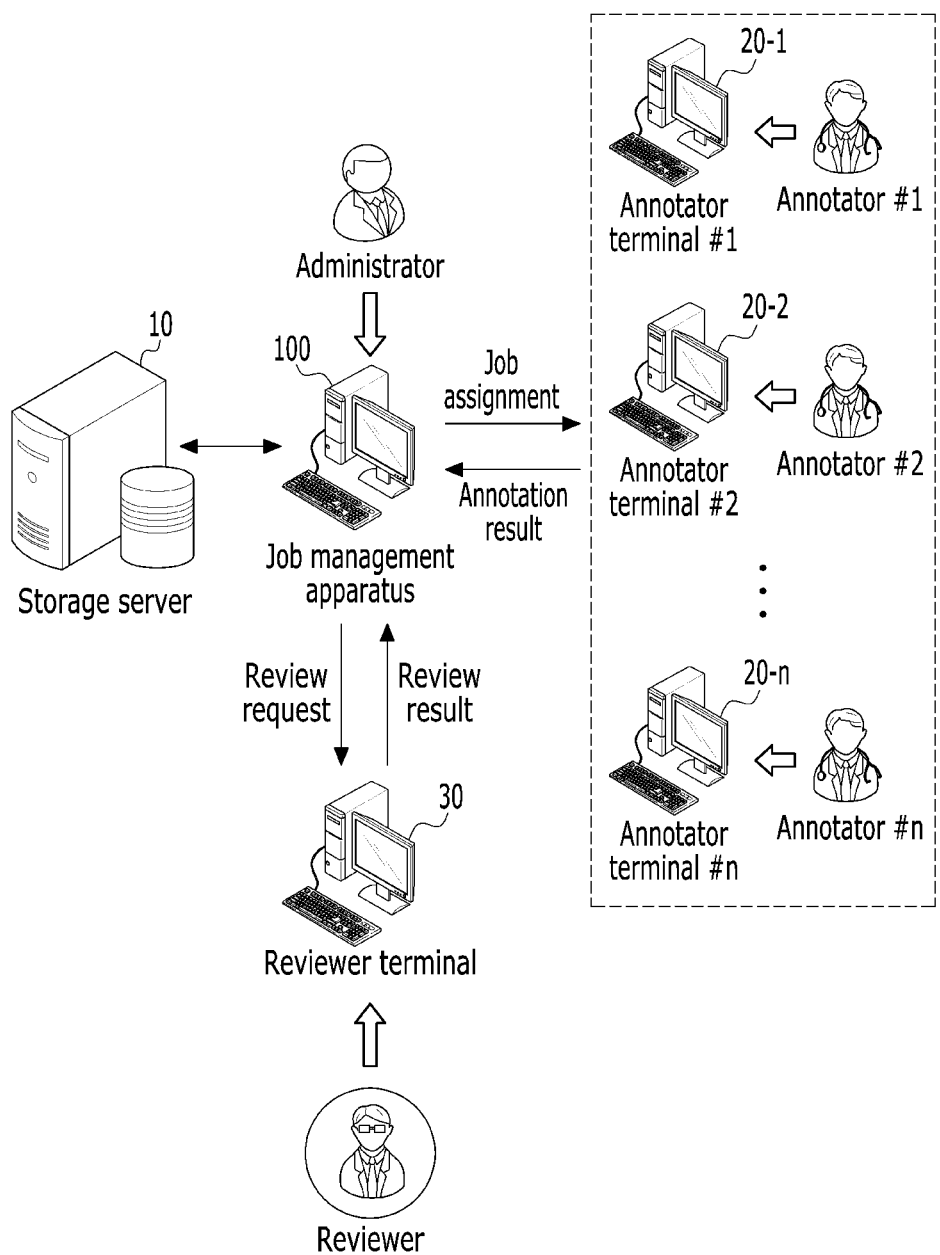

The elements of the system shown in FIG. 2 or FIG. 3 represent functional elements that are classified functionally. A plurality of elements may be implemented as an integrated form in the physical environment. Alternatively, each element may be segmented into a plurality of elements according to detailed functions in the physical environment. For example, a first function of the annotation job management apparatus 100 may be implemented in a first computing device and a second function of the annotation job management apparatus 100 may be implemented in a second computing device. Hereinafter, each element is described in more detail with reference to FIG. 2 and FIG. 3.

In the annotation job management system, the storage server 10 is a server that stores and manages various data associated with an annotation job. In order to manage data effectively, the storage server 10 may store and manage the various data using a database.

The various data may include a medical slide image file, metadata of the medical slide image (e.g. an image format, a name of related disease, a related tissue, related patient information, and the like), data about the annotation job, data about an annotator, and a result of the annotation job. However, the technical concept of the present disclosure is not limited thereto.

In some embodiments, the storage server 10 may function as a web server that presents a job management web page. In this case, through the job management web page, an administrator may perform job management such as assigning an annotation job, and the annotator may recognize and perform the assigned job.

Figure 4:
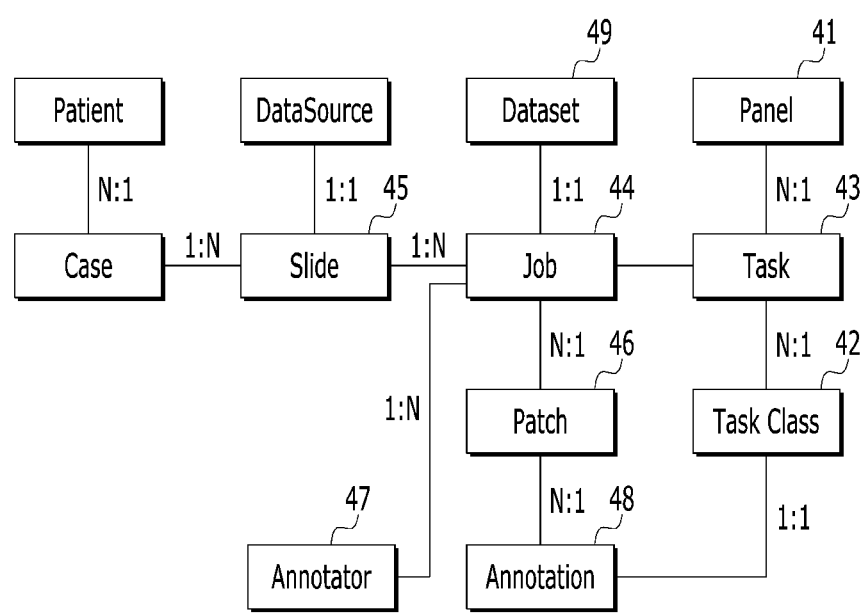
FIG. 4 is a diagram of an example data model for annotation job management according to some embodiments of the present disclosure.

In some embodiments, a data model (e.g. DB schema) for the annotation job management may be designed as shown in FIG. 4. In FIG. 4, a box-shaped object refers to an entity, a line connecting box-shaped objects refers to a relationship, and letters on the line refer to a relationship type. As shown in FIG. 4, an annotation job entity 44 may be associated with various entities 43, 45, 46, 47, and 49. Hereinafter, for convenience of understanding, the data model shown in FIG. 4 is briefly described centered on the job entity 44.

A slide entity 45 is an entity related to a medical slide image. The slide entity 45 may have various information associated with the medical slide image as attributes. Since a plurality of annotation jobs may be generated from one medical slide image, a relationship between the slide entity 45 and the job entity 44 is 1:n.

A dataset entity 49 is an entity that represents a use of the annotated data. For example, the use may be classified into a training use (that is, utilized as a training dataset), a validation use (that is, utilized as a validation dataset), a test use (that is, utilized as a test dataset), or an OPT (Observer Performance Test) use (that is, utilized in the OPT test), but the technical concept of the present disclosure is not limited thereto.

An annotator entity 47 is an entity that represents an annotator. The annotator entity 47 may have as attributes, such as a current job status of the annotator, a job history performed previously, an evaluation result of the previously-performed job, personal information of the annotator (e.g., education, major, etc.), and the like. Since one annotator can perform multiple jobs, a relationship between the annotator entity 47 and the job entity 44 is 1:n.

A patch entity 46 is an entity associated with a patch derived from the medical slide image. Since the patch may include a plurality of annotations, a relationship between the patch entity 46 and an annotation entity 48 is 1:n. Furthermore, since one annotation job may be performed on a plurality of patches, a relationship between the patch entity 46 and the job entity 44 is n:1.

An annotation task entity 43 represents an annotation task that is a detailed type of the annotation job. For example, the annotation task is defined and categorized as a task of tagging whether a specific cell is a mitotic cell, a task of tagging the number of mitotic cells, a task of tagging a type of a lesion, a task of tagging a location of the lesion, a task of tagging a name of disease, or the like. The detailed types of the annotation job can vary according to panels (that is, an annotation tagged on the cell panel may be different from an annotation tagged on the tissue panel). Since different tasks can be performed on the same panel, the task entity 43 may have a panel entity 41 and a task class entity 42 as attributes. Here, the task class entity 42 represents an annotation target (e.g., the mitotic cell, the location of the lesion) defined from a perspective of the panel or an annotation type defined from a perspective of the panel. Since multiple annotation jobs can be generated from one annotation task (that is, there can be multiple jobs performing the same task), a relationship between the annotation task entity 43 and the annotation job entity 44 is 1:n. From a programming point of view, the annotation task entity 43 may correspond to a class or a program, and the annotation job entity 44 may correspond to an instance of the class or to a process generated through execution of the program.

In some embodiments, the storage server 10 may build a database based on the data model described above, and may systematically manage various data associated with the annotation job. As a result, the data management cost can be reduced and the overall work process of annotation can be facilitated.

The data model for the annotation job management has been described above. Next, each element of the annotation job management system is continuously described with reference to FIG. 2 and FIG. 3.

In the annotation job management system, the annotation job management apparatus 100 is a computing device that performs various management functions such as assigning annotation jobs to the annotator terminals 20-1 to 20-n. Here, the computing device may be a tablet, a desktop, a laptop, or the like but is not limited thereto, and may include any kind of device having computing functions. An example of the computing device will be described with reference to FIG. 24. In the following description, for convenience of description, the annotation job management apparatus 100 is referred to as a "management apparatus" 100. In addition, when annotator terminals are designated collectively or a certain annotator terminal is designated, a reference numeral 20 is used.

The job management apparatus 100 may be a device used by an administrator. For example, through the job management apparatus 100, the administrator may access the job management web page, log in with an administrator account, and then perform overall management on the annotation jobs. For example, the manager may perform management such as assigning an annotation job to a specific annotator or requesting a review by transmitting the annotation result to the reviewer's account. The overall management process as described above may be automatically performed by the job management apparatus 100, which will be described with reference to FIG. 5.

Figure 7:
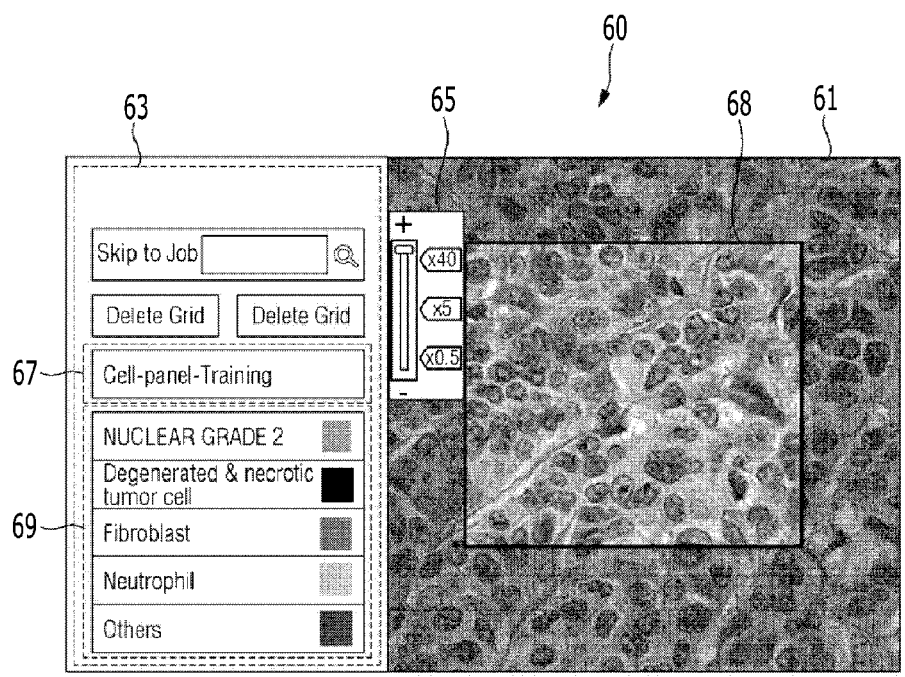
FIG. 7 is an example diagram showing an annotation tool to be referred in some embodiments of the present disclosure.

In the annotation job management system, the annotator terminal 20 is a terminal on which the annotation task is performed by the annotator. An annotation tool may be installed in the terminal 20. Various functions for annotation may be provided through the job management web page. In this case, the annotator may access the job management web page through the terminal 20 and then perform the annotation job on the web. An example of the annotation tool is shown in FIG. 7.

In the annotation job management system, the reviewer terminal 30 is a terminal of the reviewer to perform a review on the annotation result. The reviewer may review the annotation result using the reviewer terminal 30, and provide a review result to the management apparatus 100.

In some embodiments, at least some elements of the annotation job management system may communicate over a network. Here, the network may be implemented by using any type of wired/wireless network such as a local area network (LAN), a wide area network (WAN), a mobile radio communication network, a wireless broadband Internet (Wi-bro), or the like.

The annotation job management system according to some embodiments of the present disclosure has been described above with reference to FIG. 2 to FIG. 4. Hereinafter, an annotation job management method according to some embodiments of the present disclosure is described with reference to FIG. 5 to FIG. 23.

Each step of the annotation job management method may be performed by a computing device. In other words, each step of the annotation job management method may be implemented as one or more instructions to be executed by a processor of the computing device. For convenience of understanding, the description is continued on the assumption that the annotation job management method is performed in an environment shown in FIG. 3 or FIG. 4.

Figure 5:
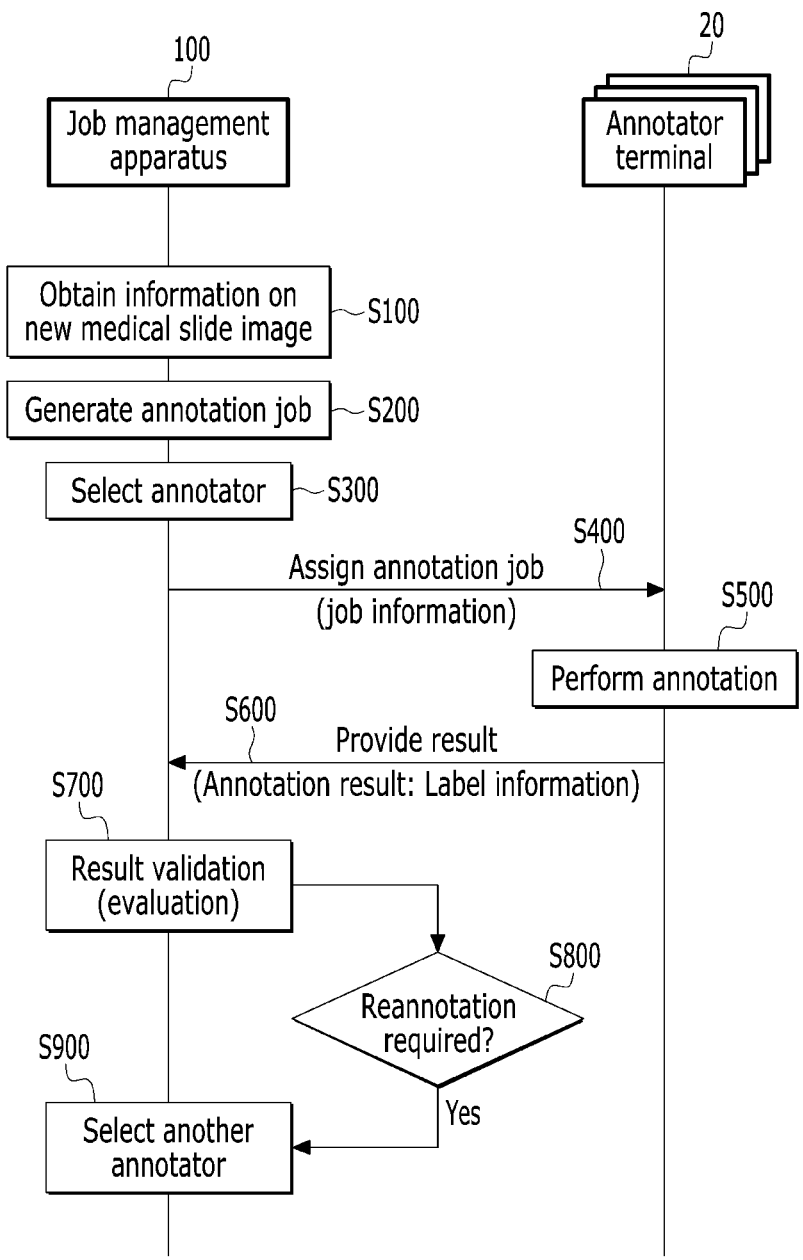
FIG. 5 is an example flowchart showing an annotation job management method according to some embodiments of the present disclosure.

FIG. 5 is an example flowchart showing an annotation job management method according to some embodiments of the present disclosure. The flowchart merely corresponds to an example embodiment for achieving an object of the present disclosure, and some steps may be added or omitted as necessary.

As shown in FIG. 5, the annotation job management method begins with step S100 of acquiring information about a new medical slide image. The information about the medical slide image may include metadata of the medical slide image, and may further include a medical slide image file.

In some embodiments, the information about the new medical slide image may be obtained through a worker agent in real time. More specifically, the worker agent may detect that the medical slide image file is added on the storage that is designated by the worker agent (that is, a storage server 10 or a storage of a medical institution providing the medical slide image). In addition, the worker agent may insert the information about the new medical slide image into a database of the job management apparatus 100 or the storage server 10. Then, the information about the new medical slide image may be obtained from the database.

In step S200, the management apparatus 100 generates an annotation job for the medical slide image. Here, the annotation job may be defined based on information such as the medical slide image, a dataset type, an annotation task, and a patch which is a partial area of the medical slide image (that is, an annotation target area) (refer to FIG. 4). A detailed description of step S200 will be described with reference to FIG. 8 to FIG. 23.

In step S300, the management apparatus 100 selects an annotator to perform the generated annotation job.

Figure 6:
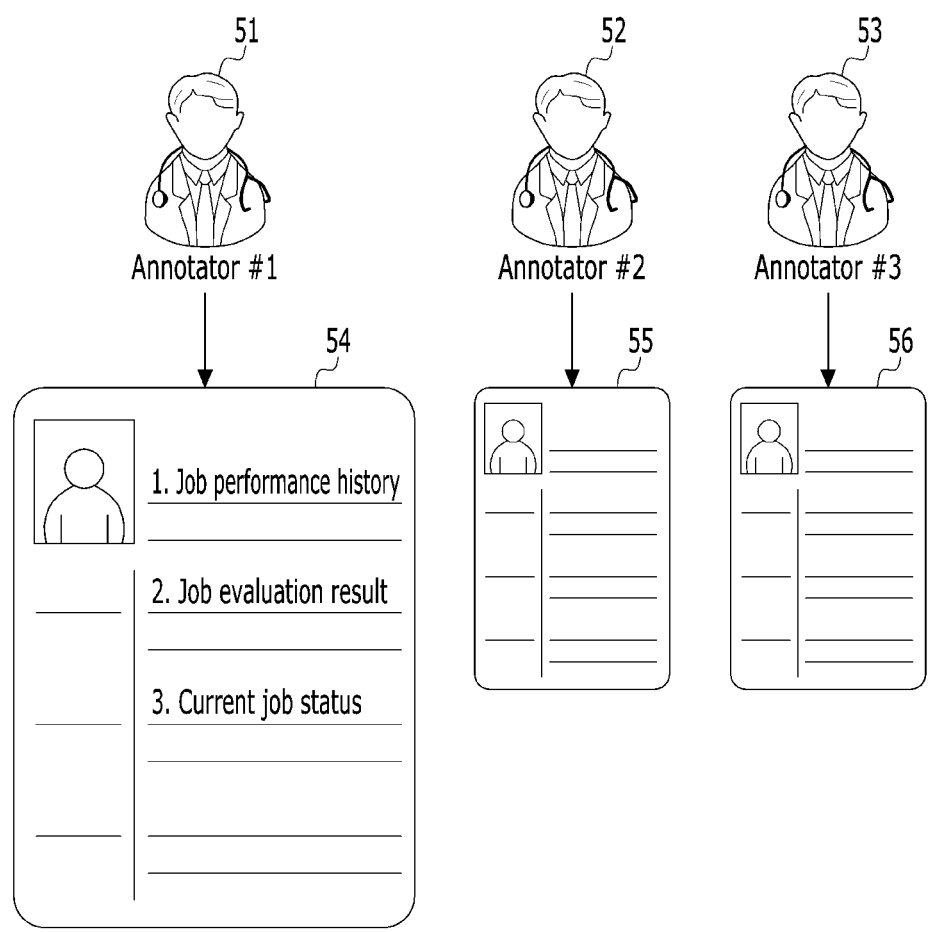
FIG. 6 is an example diagram for explaining an annotator selection method according to some embodiments of the present disclosure.

In some embodiments, as shown in FIG. 6, the management apparatus 100 may select the annotator based on management information such as a job performance history 54 (e.g., annotation jobs frequently performed by a specific annotator), evaluation results (or verification results) 55 of previously-performed jobs, and a current job status 56 (e.g., a progress status of the currently assigned job). For example, the management apparatus 100 may select a first annotator who has frequently performed a job associated with the generated annotation job, a second annotator with high performance on the job associated with the generated annotation job, or a third annotator who currently has a small workload, as the annotator for the generated annotation job.

In one embodiment, whether the job performance history includes the job associated with the generated annotation job may be determined based on whether a combination of a dataset type and a panel of an annotation task in each job is similar to a combination of those in the generated annotation job. In another embodiment, it may be determined based on whether a combination of the panel and a task class of the annotation task in each job is similar to a combination of those in the generated annotation job. In yet another embodiment, it may be determined based on whether the above-described two combinations are similar to those in the generated annotation job.

In some embodiments, when the new medical slide image is significant data (e.g. a slide image associated with rare disease, a high quality slide image, and the like.), a plurality of annotators may be selected. In addition, the number of the annotators may be increased in proportion to the significance. In this case, verification of the annotation results may be performed by comparing the respective annotation results of the plurality of annotators with each other. According to the present embodiment, through more strict verification on the significant data, the accuracy of annotation results can be improved.

In step S400, the management apparatus 100 assigns the annotation job to the terminal 20 of the selected annotator. For example, the management apparatus 100 may assign the annotation job to an account of the selected annotator.

In step S500, an annotation is performed on the annotator terminal 20. The annotator may perform the annotation using an annotator tool provided in the terminal 20 or an annotation service provided through web (e.g., a job management web page), but the technical scope of the present disclosure is not limited thereto.

Some examples of the annotator tools are shown in FIG. 7. As shown in FIG. 7, the annotation tool 60 may include a first area 63 and a second area 61. The second area 61 may include a patch area 68 on which an annotation is performed and an enlargement/reduction indicator 65. As shown in FIG. 7, the patch area 68 may be highlighted, for example, by using a box line or the like. Job information 67 is displayed in the first area 63, and a tool area 69 may be further included in the first area 63. The tool area 69 may include selectable tools corresponding to each type of annotation. Thus, each annotator can tag an annotation in the patch area 68 simply using a selected tool (e.g., perform tagging by selecting a first tool by click and then clicking the patch area 68) without directly noting the annotation in the patch area 68. Since the type of annotation displayed in the tool area 63 may vary depending on the annotation job, the annotation tool 60 may set appropriate annotation tools based on the information about the annotation job.

It should be understood that the annotation tool 60 shown in FIG. 7 only shows one example of a tool designed for convenience of the annotator. In other words, the annotation tool can be implemented in any way. The description is continued with reference to FIG. 5 again.

In step S600, the annotator terminal 20 provides a result of the annotation job. The result of the annotation job may be label information tagged to the corresponding patch.

In step S700, the management apparatus 100 performs validation (evaluation) on the job result. The validation result may be recorded as an evaluation result of the annotator. A method for validation may vary according to embodiments.

In some embodiments, the validation may be performed based on an output of a machine learning model. Specifically, when a first annotation result data is acquired from the annotator assigned to the job, the first annotation result data may be compared with a result obtained by inputting a patch of the annotation job to the machine learning model. As a result of the comparison, if it is determined that a difference between the two results exceeds a reference value, the first annotation result data may be suspended or disapproved.

In one embodiment, the reference value may be a predetermined fixed value or a variable value according to a condition. For example, the reference value may be smaller as the accuracy of the machine learning model is higher.

In step S800, the management apparatus 100 determines whether the annotation job should be performed again. For example, when the validation result indicates that the annotation job is not performed successfully in step S700, the management apparatus 100 may determine that the annotation job needs to be performed again.

In step S900, in response to the determination, the management apparatus 100 selects other annotator and reassigns the annotating job to the other annotator. In this case, the other annotator may be selected through a similar way as described in step S300. Alternatively, the other annotator may be a reviewer or a machine learning model having the best performance.

Although not shown in FIG. 5, after step S900, the validation of the first annotation result data may be performed again based on a second annotation result data of the other annotator. In detail, when the second annotation result data is acquired, a similarity between the first annotation result data and the second annotation result data may be calculated. In addition, when the similarity is less than a reference value, the first annotation result data may be finally disapproved. Such the result may be recorded in the job performance history of the annotator.

An annotation job management method according to some embodiments of the present disclosure has been described above with reference to FIG. 4 to FIG. 7. According to the above-described embodiments, as the whole annotation job process can be automated, so that the convenience of the administrator can be increased and the overall work efficiency can be greatly improved. Accordingly, the time cost and human cost required for the annotation job can be greatly reduced. In addition, as the burden of annotation job is reduced, the usability of the machine learning technique can be further increased.

Furthermore, the accuracy of the annotation results can be ensured by comparing and validating the results of the annotation job with those of the machine learning model or those of other annotators. Accordingly, the performance of the machine learning model that learns the annotation results can also be improved.

Hereinafter, a detailed process of the annotation job generation step S200 is described with reference to FIG. 8 to FIG. 22.

Figure 8:
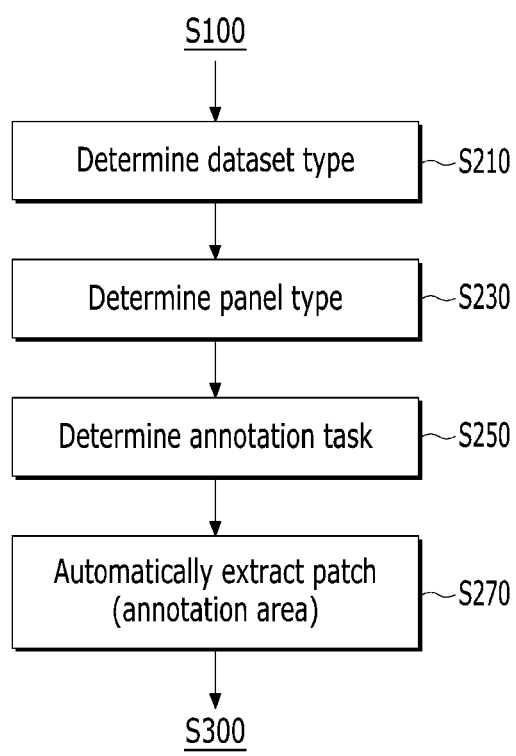
FIG. 8 is an example flowchart showing an annotation job generation method according to some embodiments of the present disclosure.

FIG. 8 is an example flowchart showing a method of generating an annotation job according to some embodiments of the present disclosure. However, the flowchart merely corresponds to an exemplary embodiment for achieving the object of the present disclosure, and some steps may be added or omitted as necessary.

As shown in FIG. 8, the method of generating an annotation job begins with step S210 of determining a dataset type of a new medical slide image. As described above, the dataset type indicates a use of the medical slide image, and the use may be classified into a training use, a validation use, a test use, or observer performance test (OPT) use.

In some embodiments, the dataset type may be determined by the administrator.

Figure 9:
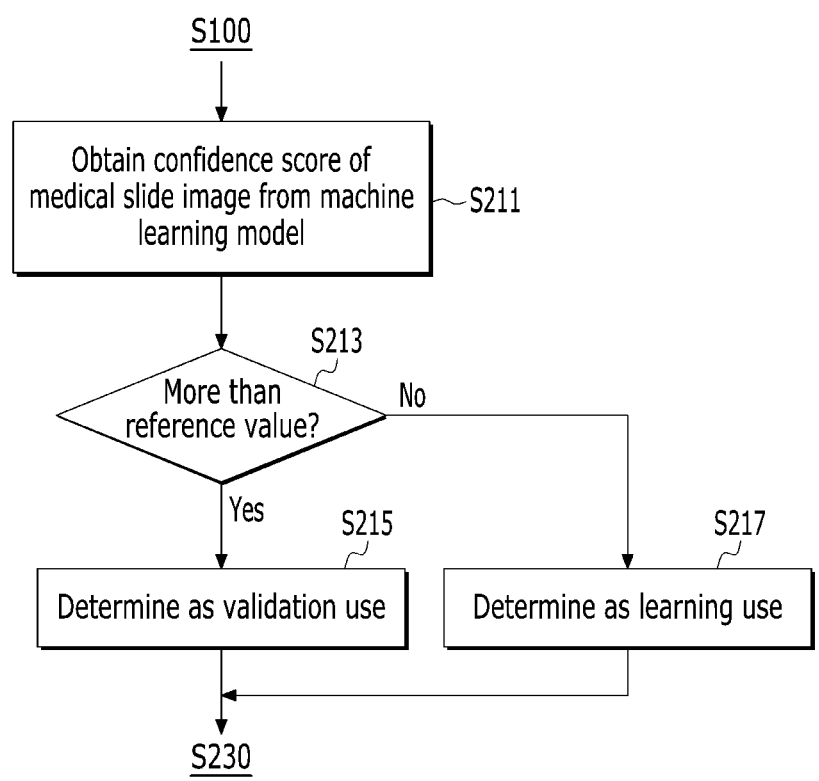
FIG. 9 is an example flowchart showing a dataset type determination method for a medical slide image according to some embodiments of the present disclosure.

In some embodiments, the dataset type may be determined based on a confidence score of a machine learning model for medical slide images. Here, the machine learning model refers to a model (that is, a learning target model) that performs a specific task (that is. lesion classification, lesion location recognition, or the like) based on the medical slide images. Details of the present embodiment are shown in FIG. 9. As shown in FIG. 9, a management apparatus 100 inputs the medical slide image into the machine learning model, acquires the confidence score as a result (S211), and determines whether the confidence score is more than or equal to a reference value (S213). In response to the determination that confidence score is less than the reference value, the management apparatus 100 determines that the dataset type of the medical slide image is the training use (S217). The confidence score being less than the reference value means that the machine learning model does not clearly interpret the medical slide image (that is, training for the medical slide image is necessary). Otherwise, the dataset type of the medical slide image is determined to be the validation use (or test use) (S215).

In some embodiments, the dataset type may be determined based on an entropy value of the machine learning model for the medical slide image. The entropy value is an indicator of uncertainty and may have a larger value as the confidence scores are distributed more evenly over the classes. In this embodiment, in response to the determination that the entropy value is more than or equal to the reference value, the dataset type may be determined to the training use. Otherwise, it may be determined to the validation use.

Referring back to FIG. 8, in step S230, the management apparatus 100 determines a panel type of the medical slide image. As described above, the panel types may be classified into a cell panel, a tissue panel, a structure panel, and the like. Example images of the cell panel type are shown in FIG. 10, example images of the tissue panel are shown in FIG. 11, and example images of the structure panel are shown in FIG. 12. As shown in FIG. 10 to FIG. 12, the cell panel is a patch type where a cell-level annotation is performed, the tissue panel is a patch type where a tissue-level annotation is performed, and the structure panel is a patch type where an annotation, which is associated with a structure of a cell or tissue, is performed.

In some embodiments, the panel type may be determined by the administrator.

Figure 13:
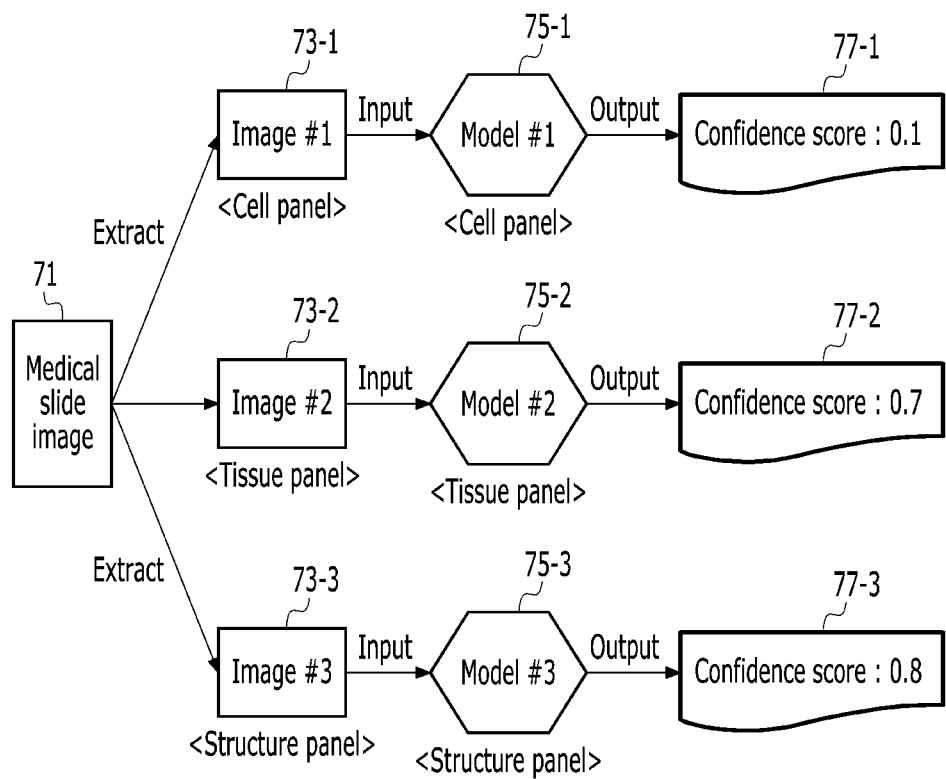

In some embodiments, the panel type may be determined based on an output value of the machine learning model. Referring to FIG. 13, the machine learning model may include a first machine learning model 75-1 corresponding to a cell panel (that is, a model that learns a cell-level annotation) and a second machine learning model 75-2 corresponding to a tissue panel, and a third machine learning model 75-3 corresponding to a structure panel. In this case, the management apparatus 100 may extract (or sample) first, second, and third images 73-1, 73-2, and 73-3 corresponding to the respective panels from a given medical slide image 71, input each of the first, second, and third images 73-1, 73-2, and 73-3 to each of the corresponding models 75-1, 75-2, and 75-3, and may obtain output values 77-1, 77-2, and 77-3 as results. In addition, the management apparatus 100 may determine the panel type of the medical slide image 71 by comparing the output values 77-1, 77-2, and 77-3 with a reference value. For example, when the first output value 77-1 is less than the reference value, the panel type of the medical slide image 71 may be determined as the cell panel. This is because cell patches extracted from the medical slide image 71 can effectively improve the learning performance of the first machine learning model 75-1.

In some embodiments, the medical slide image may have a plurality of panel types. In this case, patches corresponding to each panel may be extracted from the medical slide image.

Referring back to FIG. 8, in step S250, the management apparatus 100 determines an annotation task. As described above, the annotation task indicates an entity defined by the detailed job type.

In some embodiments, the annotation task may be determined by the administrator.

In some embodiments, the annotation task may be automatically determined based on a combination of the determined dataset type and panel type. For example, when the annotation task corresponding to the combination of the dataset type and the panel type is predefined, the corresponding annotation task may be automatically determined based on the combination.

In step S270, the management apparatus 100 automatically extracts a patch on which the annotation is actually to be performed, from the medical slide image. In some embodiments, an area designated by the administrator may be extracted as the patch. A specific method of automatically extracting the patch may vary depending on embodiments, and various embodiments related to the patch extraction will be described with reference to FIG. 14 to FIG. 23.

In some embodiments, although not shown in FIG. 8, after step S270, the management apparatus 100 may generate an annotation job based on the dataset type, panel type, annotation task, and patch determined in steps S210 to S270. As described above, the generated annotation job may be assigned to an account of an appropriate annotator.

The method of generating the annotation job according to some embodiments of the present disclosure has been described above with reference to FIG. 8 to FIG. 13. Hereinafter, various embodiments of the present disclosure related to automatic patch extraction are described with reference to FIG. 14 to FIG. 23.

Figure 14:
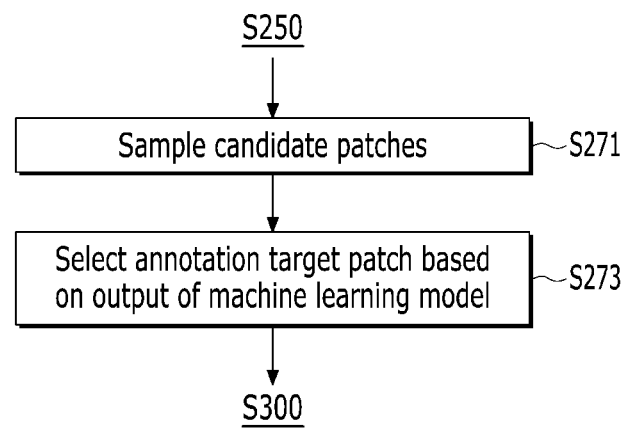
FIG. 14 is an example flowchart showing an automatic patch extraction method according to a first embodiment of the present disclosure.

FIG. 14 is an example flowchart showing an automatic patch extraction method according to a first embodiment of the present disclosure. However, the flowchart merely corresponds to an exemplary embodiment for achieving the object of the present disclosure, and some steps may be added or omitted as necessary.

As shown in FIG. 14, the automatic patch extraction method begins with step S271 of sampling a plurality of candidate patches in a new medical slide image. A specific process of sampling the plurality of candidate patches may vary depending on embodiments.

Figure 15:
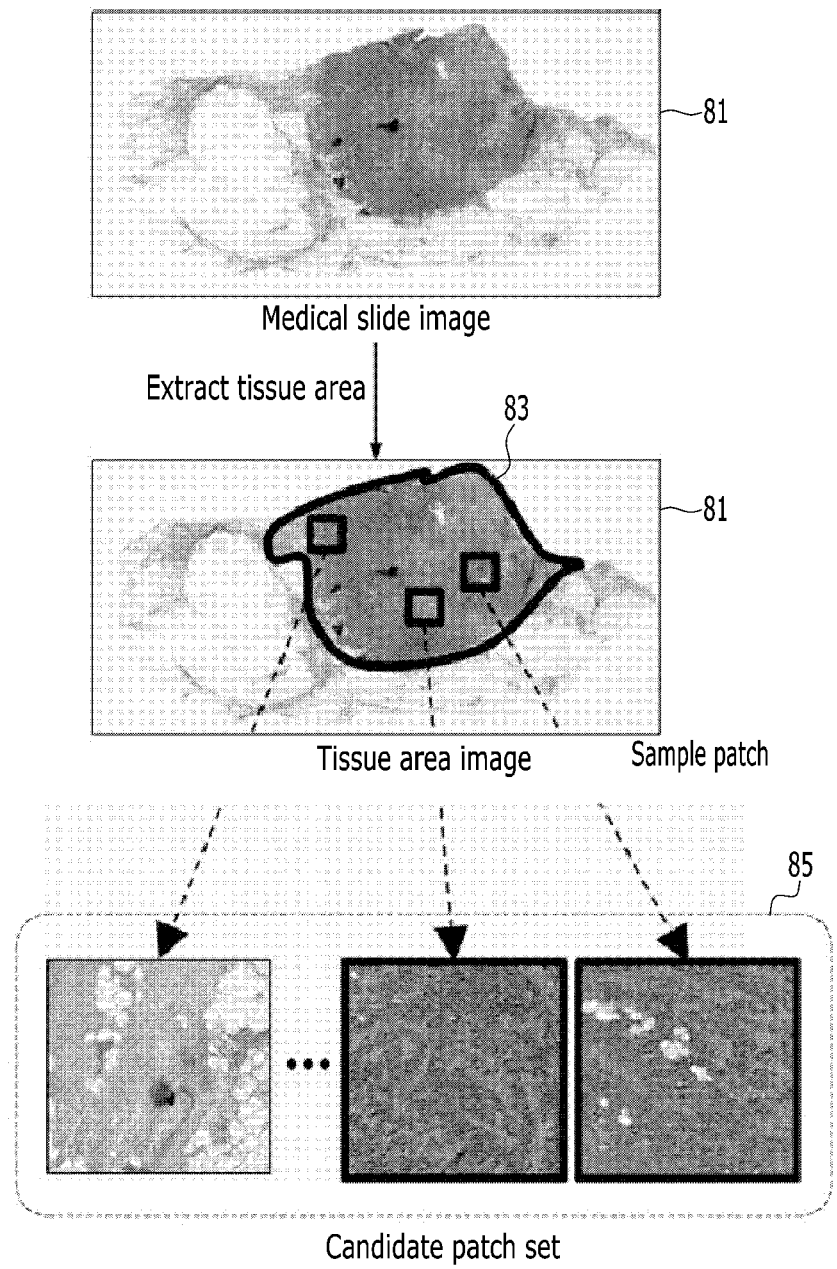
FIG. 15, FIG. 16, FIG. 17, FIG. 18, and FIG. 19 are example diagrams for explaining an automatic patch extraction method according to a first embodiment of the present disclosure.
Figure 16:
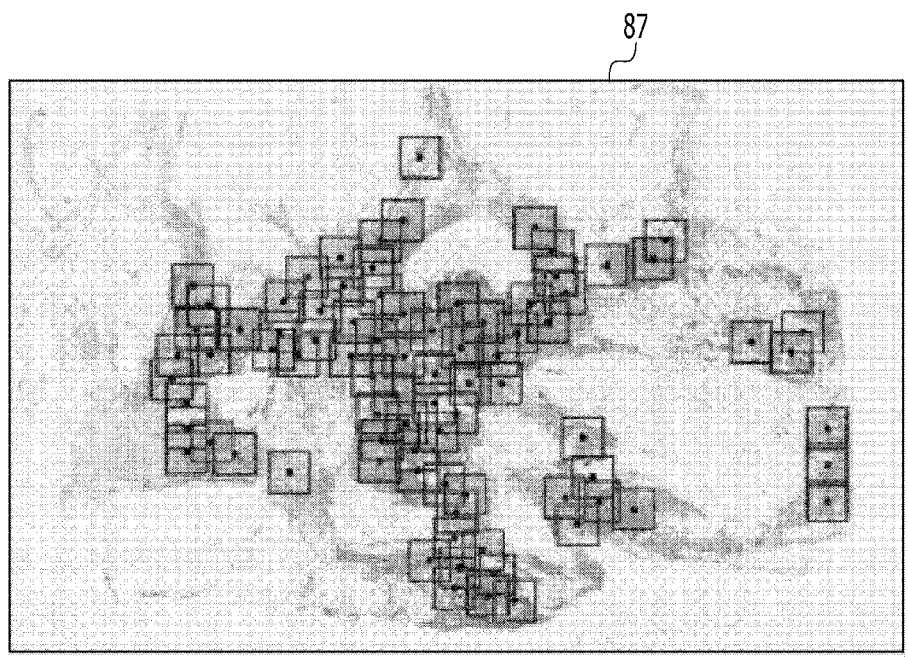
Figure 17:
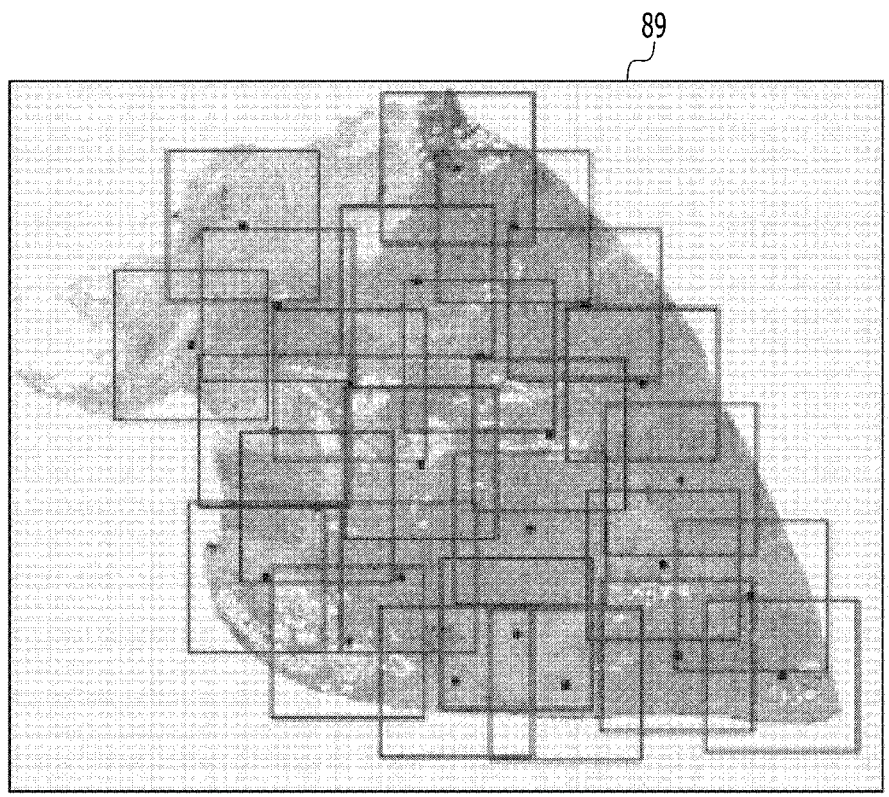

In some embodiments, in a case that at least cell regions constituting a specific tissue are sampled as candidate patches (that is, patches of a cell panel type), a tissue area 83 may be extracted from a medical slice image 81 through image analysis, and a plurality of candidate patches 85 may be sampled within the extracted area 83, as shown in FIG. 15. Some examples of sampling results are shown in FIG. 16 and FIG. 17. In medical slide images 87 and 89 shown in FIG. 16 and FIG. 17, each point refers to a sampling point and each of rectangular figures refers to a sampling area (that is, a candidate patch area). As shown in FIG. 16 and FIG. 17, the plurality of candidate patches may be sampled in such a manner that at least some of the candidate patches overlap with one another.

In some embodiments, the candidate patches may be generated by uniformly dividing an entire area of a medical slide image and then sampling each of the divided areas. That is, the sampling may be performed in an equally dividing manner In this case, the size of each candidate patch may be a predetermined fixed value, or a variable value determined based on a size, resolution, panel type, or the like of the medical slide image.

In some embodiments, the candidate patches may be generated by randomly dividing the entire area of the medical slide image and then sampling each of the divided areas.

In some embodiments, the candidate patches may be configured such that the number of objects exceeds a reference value. For example, object recognition may be performed on the entire area of the medical slide image, and, as a result, an area having a larger number of objects, which are calculated as a result of the object recognition, than the reference value may be sampled as a candidate patch. In such a case, the sizes of the candidate patches may be different.

In some embodiments, the candidate patches that are divided according to a policy determined based on metadata of the medical slide image may be sampled. Here, the metadata may be a disease name, tissue or demographic information of a patient associated with the medical slide image, a location of a medical institution, a quality (e.g. resolution) or format type of the medical slide image, or the like. For example, when the medical slide image is an image about a tissue of a tumor patient, candidate patches may be sampled at cell level to be used as training data of a machine learning model for mitotic cell detection. In another example, in a case that lesion location in the tissue is critical when the prognosis of disease associated with the medical slide image is diagnosed, candidate patches may be sampled at tissue level.

In some embodiments, when sampling candidate patches of the structure panel type in the medical slide image, outlines are extracted from the medical slide image through image analysis, and sampling may be performed so that the outlines that are connected to each other among the extracted outlines form one candidate patch.

As described above, a specific method of sampling a plurality of candidate patches in step S271 may vary depending on embodiments. The description is continued referring back to FIG. 14.

In step S273, an annotation target patch is selected based on an output value of the machine learning model. The output value may be, for example, a confidence score (or a confidence score of each class), and a specific method of selecting a patch based on the confidence score may vary depending on embodiments.

In some embodiments, the annotation target patch may be selected based on the entropy value calculated by the confidence score for each class. Details of the present embodiment are shown in FIG. 18 and FIG. 19.

Figure 18:
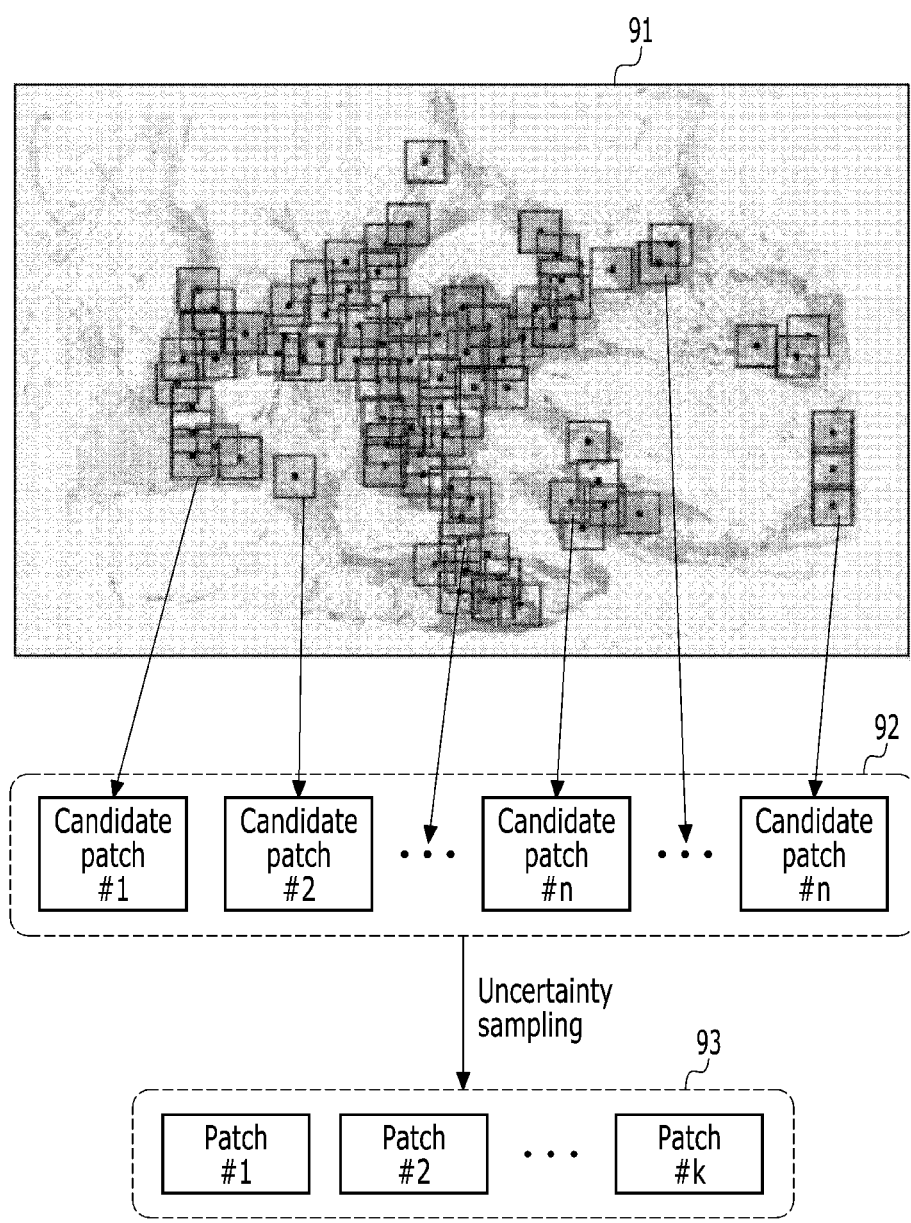
Figure 19:
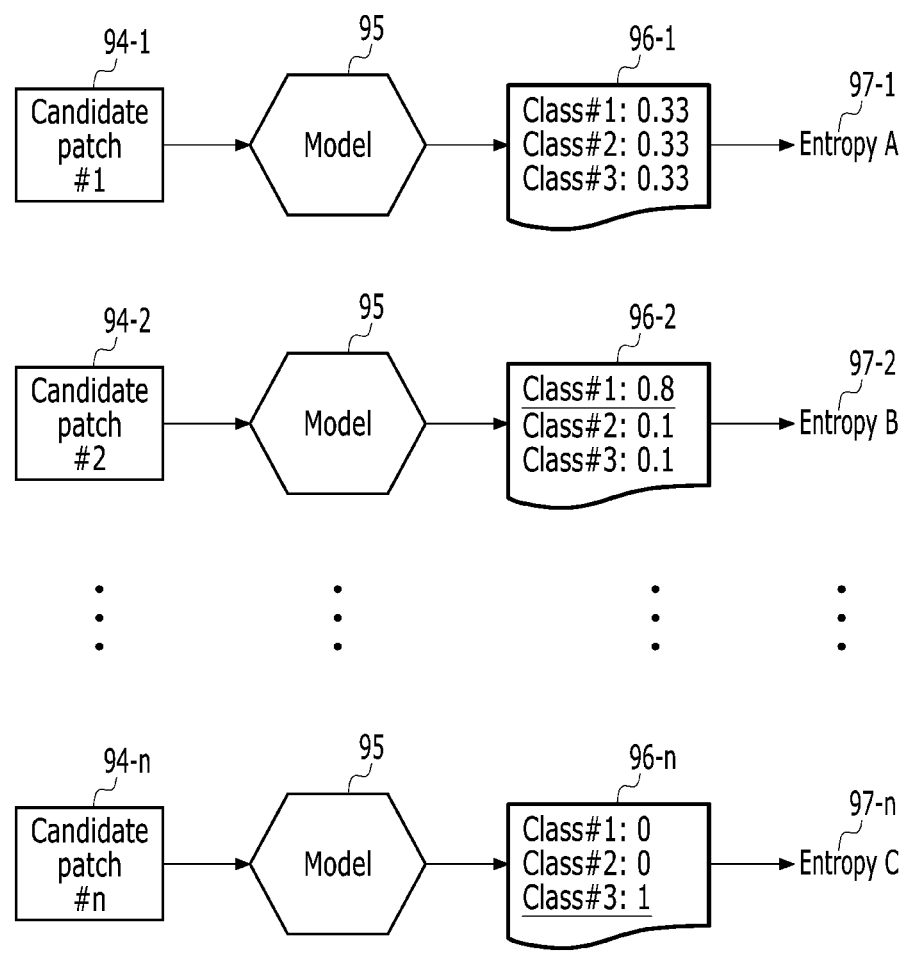

As shown in FIG. 18, annotation target patches 93 may be selected from candidate patches 92 that are sampled in a medical slide image 91, through uncertainty sampling based on entropy values. More specifically, as shown in FIG. 19, entropy values 97-1 to 97-$n$ may be calculated based on confidence scores for each class 96-1 to 96-$n$ of candidate patches 94-1 to 94-$n$ that are output from a machine learning model 95. As described above, the entropy value has a larger value as the confidence scores are more evenly distributed over classes. For example, in the case shown in FIG. 19, entropy A (97-1) has the largest value and entropy C (97-$n$) has the smallest value. In addition, the candidate patches which have larger entropy value than a reference value may be automatically selected as the annotation target. The patch having the larger entropy value means that prediction results of the machine learning model are uncertain, which means that the patch is more effective data for training.

In some embodiments, the annotation target patch may be selected based on the confidence score itself. For example, among a plurality of the candidate patches, a candidate patch having a confidence score less than a reference value may be selected as the annotation target patch.

Figure 20:
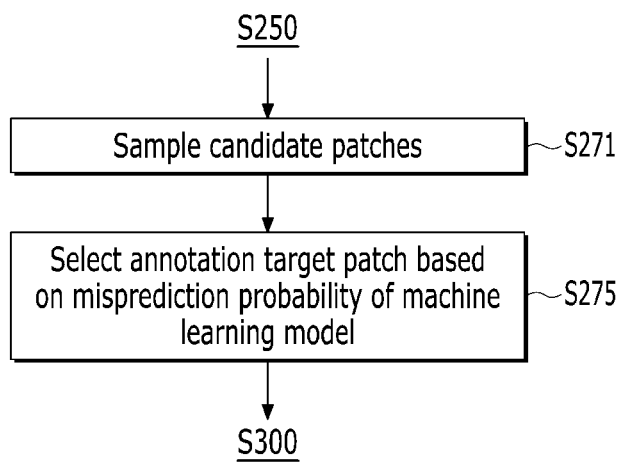
FIG. 20 is an example flowchart showing an automatic patch extraction method according to a second embodiment of the present disclosure.

FIG. 20 is an example flowchart showing an automatic patch extraction method according to a second embodiment of the present disclosure. However, the flowchart shown in FIG. 20 merely corresponds to an exemplary embodiment for achieving an object of the present disclosure, and some steps may be added or omitted as necessary. For convenience of description, repeated descriptions of the above described embodiments are omitted.

As shown in FIG. 20, the second embodiment also begins with step S271 of sampling a plurality of candidate patches. However, differently from the first embodiment, in the second embodiment, the annotation target patch is selected based on a misprediction probability of a machine learning model (S275).

The misprediction probability of the machine learning model may be calculated based on a misprediction probability calculation model (hereinafter, referred as "calculation model") that is constructed through machine learning. For convenience of understanding, a method of construction the calculation model is described with reference to FIG. 21 and FIG. 22.

Figure 21:
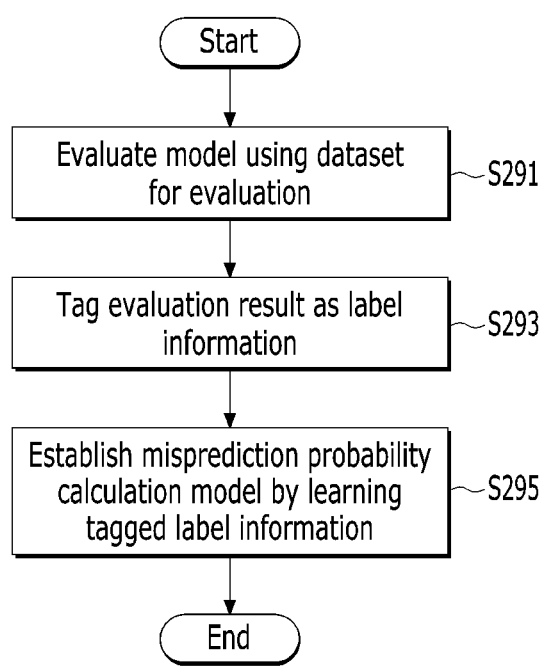
FIG. 21, FIG. 22, and FIG. 23 are example diagrams for explaining an automatic patch extraction method according to a second embodiment of the present disclosure.

As shown in FIG. 21, the calculation model may be constructed by learning evaluation results (e.g. validation results and test results) of the machine learning model (S291 to S295). Specifically, when the machine learning model is evaluated with data for evaluation (S291) and the evaluation result is tagged with label information about the data for evaluation (S293), the calculation model may be constructed by learning the tagged label information on the data for evaluation (S295).

Figure 22:
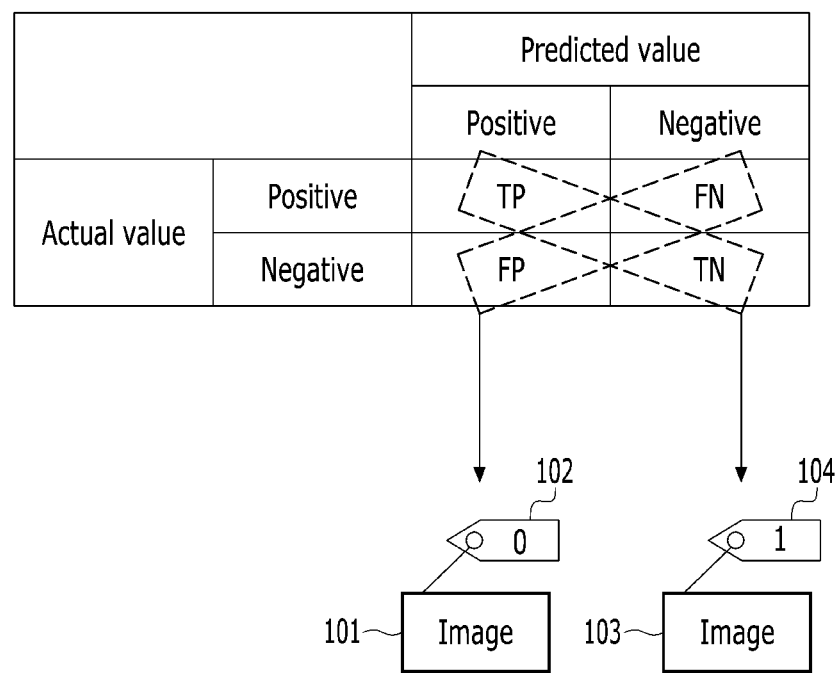

Some examples of tagging label information to the data for evaluation are shown in FIG. 22. FIG. 22 represents a confusion matrix. When the machine learning model is a model for performing a classification task, the evaluation result may correspond to a specific cell in the confusion matrix. As shown in FIG. 22, a first value (e.g., 0) is tagged as a label 102 on an image 101 which has an evaluation result of FP (false positive) or FN (false negative), and a second value (e.g., 1) is tagged as a label 104 on an image 103 which has an evaluation result of TP (true positive) of TN (true negative). That is, when the prediction of the machine learning model is a correct answer, "1" may be tagged, and, otherwise, "0" may be tagged.

After learning the images 101 and 102 and the label information thereof, the calculation model outputs a high confidence score when an image similar to the image correctly predicted by the machine learning model is input and, otherwise, outputs a low confidence score. Therefore, the calculation model can calculate a misprediction probability of the machine learning model for the input image.

Meanwhile, FIG. 22 merely shows some example for tagging the label information. According to some embodiments of the present disclosure, a prediction error may be tagged as label information. Here, the prediction error represents a difference between a predicted value (that is, confidence score) and an actual value (that is, correct answer information).

Further, according to some embodiments of the present disclosure, a first value (e.g., 0) may be tagged when the prediction error of an image for evaluation is greater than or equal to a reference value, and otherwise a second value (e.g., 1) may be tagged.

Referring back to FIG. 20, the description will be continued.

When the calculation model is constructed according to above-described process, in step S275, the management apparatus 100 may calculate a misprediction probability for each of the plurality of candidate patches. For example, as shown in FIG. 23, the management apparatus 100 inputs each of data samples 111-1 to 111-$n$ into a calculation model 113 to obtain the confidence score 115-1 to 115-$n$ of the calculation model 113, and calculates the misprediction probability based on the obtained confidence scores 115-1 to 115-$n$.

Figure 23:
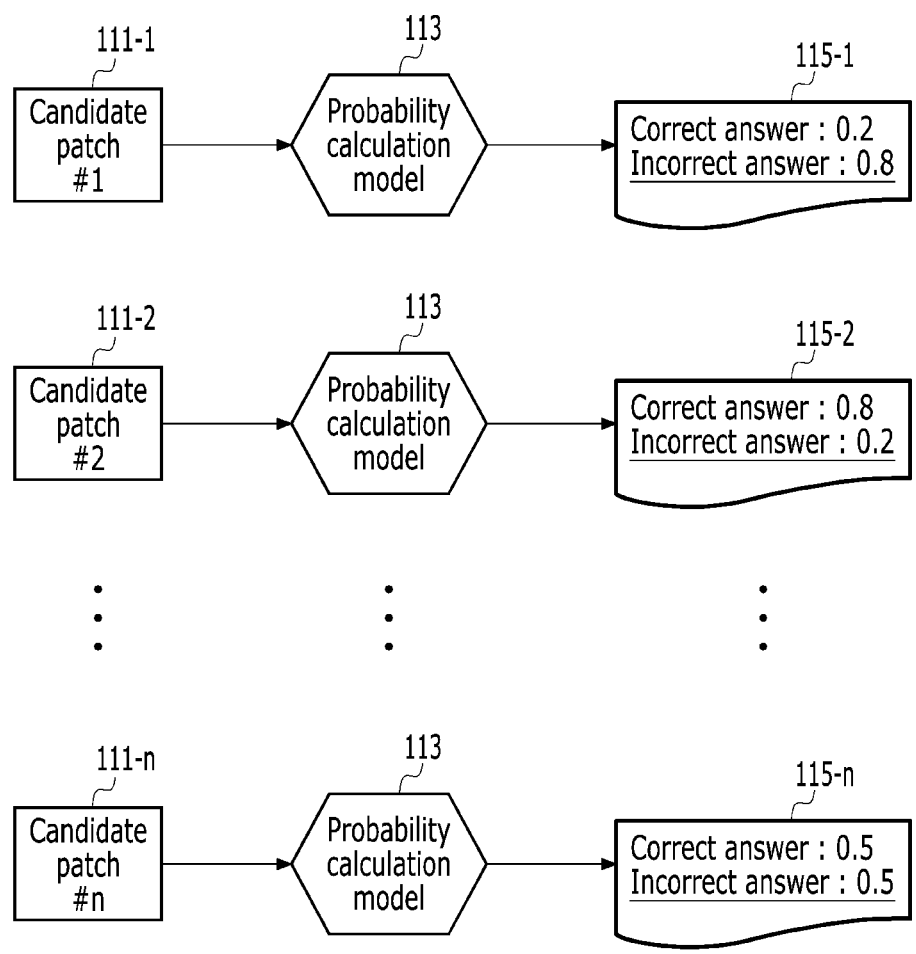

However, as shown in FIG. 23, when the candidate patches 111-1 to 111-$n$ are input, in a case that the calculation model 113 has been learned to output the confidence scores 115-1 to 115-$n$ for each of correct classes and incorrect classes (that is, in a case that the calculation model has been learned to tag label "1" when the prediction matches the correct answer, and otherwise to tag label "0"), the confidence scores of the incorrect classes (shown as underlined) may be used as the misprediction probability.

When the misprediction probability of each of the candidate patches is calculated, the management apparatus 100 may select as the annotation target a candidate patch, having a calculated misprediction probability equal to or greater than a reference value, from the plurality of candidate patches. A high misprediction probability means that the prediction results of the machine learning model are likely to be incorrect since the corresponding patches are important data for improving the performance of the machine learning model. Thus, when patches are selected based on the misprediction probability, high-quality training datasets may be generated because the patches effective for learning are selected as the annotation targets.

The automatic patch extraction method according to various embodiments of the present disclosure has been described above with reference to FIG. 14 to FIG. 23. According to the above-described method, patches indicating areas where annotations are to be performed can be automatically extracted. Therefore, the workload of the administrator can be minimized In addition, since only patches effective for learning among a plurality of candidate patches are selected as annotation targets based on misprediction probability or entropy values of the machine learning model, the amount of annotation job can be reduced, and a high-quality training dataset can be generated.

Hereinafter, an example computing device 200 that may implement an apparatus (e.g. management apparatus 100)/system according to various embodiments of the present disclosure will be described with reference to FIG. 24.

Figure 24:
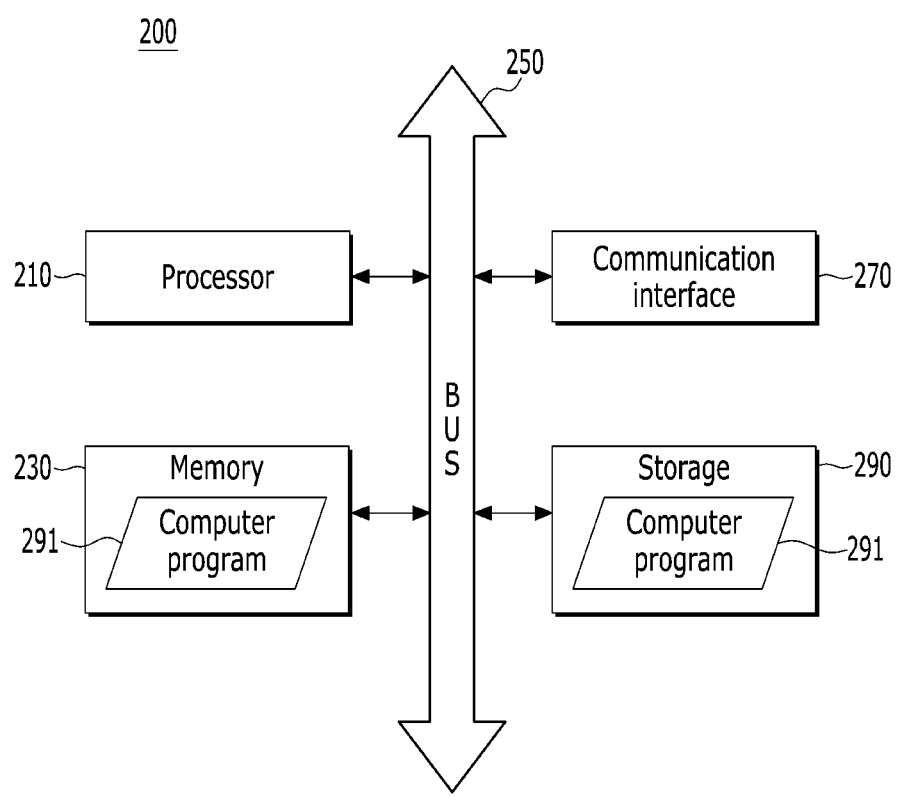
FIG. 24 is an example computing device for implanting an apparatus/system according to various embodiments of the present disclosure.

FIG. 24 is an example hardware block diagram illustrating an example computing device 200 that can implement an apparatus according to various embodiments of the present disclosure.

As shown in FIG. 24, the computing device 200 may include one or more processors 210, a bus 250, a communication interface 270, a memory 230 to which a computer program executed by the processor 210 is loaded, and a storage 290 that stores a computer program 291. However, FIG. 24 shows merely elements related to the embodiments of the present disclosure. Therefore, the person of ordinary skill in the art will understand that general elements other that those shown in FIG. 24 may be further included.

The processor 210 controls the overall operation of each component of the computing device 200. The processor 210 may configured to include at least one of a central processing unit (CPU), a micro processor unit (MPU), a micro controller unit (MCU), a graphics processing unit (GPU), or any form of processor well known in the technical field of the present disclosure. The processor 210 may perform calculation of at least one application or program for executing methods or operations according to embodiments of the present disclosure.

The memory 230 stores various data, commands, and/or information. To execute methods or operations according to various embodiments of the present disclosure, the memory 230 may load one or more programs 291 from the storage 290. The memory 230 may be implemented as a volatile memory such as a random access memory (RAM), but the technical scope of the present disclosure is not limited thereto.

The bus 250 provides a communication function between elements of the computing device 200. The bus 250 may be implemented as various forms of buses, such as an address bus, a data bus, and a control bus, and the like.

The communication interface 270 supports wired or wireless Internet communication of the computing device 200. Further, the communication interface 270 may support various communication methods as well as Internet communication. To this end, the communication interface 270 may include a communication module well known in the technical field of the present disclosure.

The storage 290 may non-temporarily store the one or more programs 291. The storage 290 may include a non-volatile memory, such as Read Only Memory (ROM), an eraseable Programmable ROM (EPROM), an electrically erasable programmable ROM (EEPROM), and a flash memory, a hard disk, a removable disk, or any form of computer-readable recording medium well known in the art to which the present disclosure pertains.

Computer program 291 may include one or more instructions which cause the processor 210 to perform methods or operations according to various embodiments of the present disclosure by performing the one or more instructions. In other words, the processor 210 may execute methods or operations according to various embodiments of the present disclosure by performing the one or more instructions.

For example, the computer program 291 may include one or more instructions to perform an operation of obtaining information about a new medical slide image, determining a dataset type and a panel of the medical slide image, and the pathological slide image, the determined dataset type, assigning an annotation task and annotation job, which is defined by a patch that is a part of the medical slide image, to an account of an annotator. In this case, the management apparatus 100 according to some embodiments of the present disclosure may be implemented through the computing device 200.

An example computing device that may implement apparatuses according to various embodiments of the present disclosure has been described above with reference to FIG. 24.

The concepts of the disclosure described above with reference to FIG. 1 to FIG. 24 may be embodied as computer-readable code on a computer-readable medium. The computer-readable medium may be, for example, a removable recording medium (a CD, a DVD, a Blu-ray disc, a USB storage device, or a removable hard disc) or a fixed recording medium (a ROM, a RAM, or a computer-embedded hard disc). The computer program recorded on the computer-readable recording medium may be transmitted to another computing apparatus via a network such as the Internet and installed in another computing device, so that the computer program can be used in another computing device.

The technical concept of the present disclosure is not necessarily limited to these embodiments, as all the elements configuring the embodiments of the present disclosure have been described as being combined or operated in combination. That is, within the scope of the present disclosure, all of the elements may be selectively operable in combination with one or more.

Although operations are shown in a specific order in the drawings, it should not be understood that desired results can be obtained when the operations must be performed in the specific order or sequential order or when all of the operations must be performed. In certain situations, multitasking and parallel processing may be advantageous. According to the above-described embodiment, it should not be understood that the separation of various configurations is necessarily required, and it should be understood that the described program components and systems may generally be integrated together into a single software product or be packaged into multiple software products.

While the present disclosure have been particularly illustrated and described with reference to embodiments thereof, it will be understood by a person of ordinary skill in the art that various changes in form and detail may be made therein without departing from the spirit and scope of the present disclosure as defined by the following claims. The embodiments should be considered in a descriptive sense only and not for purposes of limitation.

What is claimed is:

1. An annotation job management method performed by at least one computing device, comprising:
   obtaining a medical slide image that is an annotation target;
   determining at least one of a dataset type and a panel type of the obtained medical slide image;
   selecting at least one annotation job target patch from among a plurality of candidate patches which are included in the medical slide image, based on at least one of the determined dataset type and panel type;
   assigning the at least one selected annotation job target patch to at least one annotator account;
   obtaining an annotation result for the at least one annotation job target patch from the assigned annotator account; and
   training or validating a machine learning model using a dataset generated based on the annotation result,
   wherein the panel type indicates at least one of a cell panel, a tissue panel, and a structure panel.

2. The annotation job management method of claim 1, wherein selecting the at least one annotation job target patch comprises:
   selecting the plurality of candidate patches sampled from the medical slide image;
   calculates at least one of a confidence score and an entropy value of each of the plurality of candidate patches; and
   selecting the at least one annotation job target patch based on the at least one of the confidence score and the entropy value calculated for each of the plurality of candidate patches.

3. The annotation job management method of claim 2, wherein selecting the plurality of candidate patches comprises:
   dividing at least a part of the medical slide image based on information associated with the medical slide image; and
   selecting the plurality of candidate patches from the divided at least part.

4. The annotation job management method of claim 1, wherein selecting the at least one annotation job target patch comprises:
- selecting the plurality of candidate patches sampled from the medical slide image;
- calculating a misprediction probability of the machine learning model for each of the plurality of candidate patches; and
- selecting the at least one annotation job target patch from among the plurality of candidate patches based on the calculated misprediction probability.

5. The annotation job management method of claim 1, wherein assigning the at least one annotation job target patch to the at least one annotator account comprises assigning the at least one annotation job target patch to the at least one annotator account based on at least one of the determined dataset type and panel and an annotation performance history of an annotator.

6. The annotation job management method of claim 1, further comprising:
- comparing the obtained annotation result with a result of the machine learning model for the at least one annotation job target patch; and
- determining whether to reassign the at least one annotation job target patch based on a compared result.

7. The annotation job management method of claim 1, wherein the at least one annotator account includes a plurality of annotator accounts,
- wherein obtaining the annotation result includes obtaining annotation results for the at least one annotation job target patch from the plurality of annotator accounts assigned for the at least one annotation job target patch, and
- wherein the annotation job management method further comprises:
  - comparing the annotation results of the plurality of annotator accounts; and
  - determining whether to reassign the at least one annotation job target patch based on a compared result.

8. The annotation job management method of claim 1,
- wherein the dataset type indicates a use of the medical slide image, and the use of the medical slide image includes at least one of a training use of the medical learning model and a validation use of the machine learning model.

9. The annotation job management method of claim 1, wherein determining the at least one comprises determining at least one of the dataset type and panel type of the medical slide image based on an output value outputted by inputting the medical slide image to the machine learning model.

10. An annotation job management apparatus comprising:
a memory including one or more instructions; and
a processor that, by executing the one or more instructions:
- obtains a medical slide image that is an annotation target;
- determines at least one of a dataset type and a panel type of the obtained medical slide image;
- selects at least one annotation job target patch from among a plurality of candidate patches which are included in the medical slide image, based on at least one of the determined dataset type and panel type;
- assigns the at least one selected annotation job target patch to at least one annotator account;
- obtains an annotation result for the at least one annotation job target patch from the assigned annotator account; and trains or validates a machine learning model using a training dataset generated based on the annotation result,
wherein the panel type indicates at least one of a cell panel, a tissue panel, and a structure panel.

11. The annotation job management apparatus of claim 10, wherein the processor:
- selects the plurality of candidate patches sampled from the medical slide image;
- calculates at least one of a confidence score and an entropy value of each of the plurality of candidate patches; and
- selects the at least one annotation job target patch based on the at least one of the confidence score and the entropy value calculated for each of the plurality of candidate patches.

12. The annotation job management apparatus of claim 11, wherein the processor:
- divides at least a part of the medical slide image based on information associated with the medical slide image; and
- selects the plurality of candidate patches from the divided at least part.

13. The annotation job management apparatus of claim 10, wherein the processor:
- selects the plurality of candidate patches sampled from the medical slide image;
- calculates a misprediction probability of the machine learning model for each of the plurality of candidate patches; and
- selects the at least one annotation job target patch from among the plurality of candidate patches based on the calculated misprediction probability.

14. The annotation job management apparatus of claim 10, wherein the processor assigns the at least one annotation job target patch to the at least one annotator account based on at least one of the determined dataset type and panel and an annotation performance history of an annotator.

15. The annotation job management apparatus of claim 10, wherein the processor:
- compares the obtained annotation result with a result of the machine learning model for the at least one annotation job target patch; and
- determines whether to reassign the at least one annotation job target patch based on a compared result.

16. The annotation job management apparatus of claim 10, wherein the at least one annotator account includes a plurality of annotator accounts, and
wherein the processor:
- obtains annotation results for the at least one annotation job target patch from the plurality of annotator accounts assigned for the at least one annotation job target patch;
- compares the annotation results of the plurality of annotator accounts; and
- determines whether to reassign the at least one annotation job target patch based on a compared result.

17. The annotation job management apparatus of claim 10,
wherein the dataset type indicates a use of the medical slide image, and the use of the medical slide image includes at least one of a training use of the medical learning model and a validation use of the machine learning model.

18. The annotation job management apparatus of claim 10, wherein the processor determines at least one of the dataset type and panel type of the medical slide image based on an output value outputted by inputting the medical slide image to the machine learning model.

* * * * *